(12) United States Patent
Walde

(10) Patent No.: US 6,916,415 B2
(45) Date of Patent: Jul. 12, 2005

(54) HEATER DRIVE CIRCUIT AND DRIVE METHOD FOR A GAS SENSOR

(75) Inventor: Tim Walde, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 420 days.

(21) Appl. No.: 10/156,481

(22) Filed: May 28, 2002

(65) Prior Publication Data

US 2002/0164815 A1 Nov. 7, 2002

Related U.S. Application Data

(63) Continuation of application No. PCT/DE00/04124, filed on Nov. 22, 2000.

(30) Foreign Application Priority Data

Nov. 25, 1999 (DE) .......................................... 199 56 823

(51) Int. Cl.$^7$ .......................... G01N 27/407; H05B 1/02
(52) U.S. Cl. ....................... 205/785; 204/406; 204/424; 219/497
(58) Field of Search ................................ 204/406, 424; 205/785; 73/23.31, 23.32; 123/697; 219/202, 205, 207, 497, 508

(56) References Cited

U.S. PATENT DOCUMENTS

| | | | |
|---|---|---|---|
| 4,963,246 A | | 10/1990 | Nakajima et al. |
| 4,993,392 A | * | 2/1991 | Tanaka et al. ............. 73/23.32 |
| 5,111,792 A | | 5/1992 | Nagai et al. |
| 5,279,145 A | * | 1/1994 | Suzuki ....................... 73/23.32 |
| 5,740,675 A | * | 4/1998 | Shimasaki et al. ............ 60/274 |
| 5,929,328 A | * | 7/1999 | Seidenfuss ................. 73/118.1 |

FOREIGN PATENT DOCUMENTS

| | | |
|---|---|---|
| EP | 0 067 437 A1 | 12/1982 |

OTHER PUBLICATIONS

Tietze, U. et al.: "Halbleiter–Schaltungstechnik" [Semiconductor–Circuitry], Springer–Verlag, vol. 9, 1989, pp. 890–907.

Kato, N. et al.: "Thick Film ZrOd NOx Sensor for the Measurement of Low NOx Conscentration", Society of Automotive Engineers, Inc., 1998, pp. 69–77.

Kato, N. et al.: "Performance of Thick Film NOx Sensor on Diesel and Gasoline Engines", Society Automotive Engineers, Inc., 1997, pp. 199–206.

* cited by examiner

*Primary Examiner*—Kaj K. Olsen
(74) *Attorney, Agent, or Firm*—Laurence A. Greenberg; Werner H. Stemer; Ralph E. Locher

(57) ABSTRACT

A method and device for driving a gas sensor includes a three-point circuit determining a temperature of a gas sensor having a resistive heating element by determining a measuring current with a measuring resistor flowing through the resistor in a measuring phase. The three-point measurement makes it possible to determine accurately the line resistance of an incoming line branch, which can also be used approximately for the line resistance of another incoming line branch. Naturally, the tap may also be provided on the incoming line side.

15 Claims, 2 Drawing Sheets

HEATER DRIVE CIRCUIT AND DRIVE METHOD FOR A GAS SENSOR

CROSS-REFERENCE TO RELATED APPLICATION

This application is a continuation of copending International Application No. PCT/DE00/04124, filed Nov. 22, 2000, which designated the United States and was not published in English.

BACKGROUND OF THE INVENTION

Field of the Invention

The invention relates to a drive circuit and to a method for driving a gas sensor that has a resistive heating element. A generic drive circuit and a generic method for driving are disclosed in U.S. Pat. No. 4,963,246 to Nakajima et al.

For the measurement of gas components, various gas sensors exist that need to be operated at an elevated temperature. For example, a thick film measuring detector for measuring the NOx concentration is described in the publication N. Kato et al., "Thick Film $ZrO_2$ NOx Sensor for the Measurement of Low NOx concentration", Society of Automotive Engineers, publication 980170, 1989, or in N. Kato et al., "Performance of Thick Film NOx Sensor on Diesel and Gasoline Engines", Society of Automotive Engineers, publication 970858, 1997. Such a measuring detector has two measuring cells and is of an oxygen ion conducting zirconium oxide. It implements the following measuring concept: in a first measuring cell, to which the gas to measured is sent through a diffusion barrier, a first oxygen ion pump current is used to adjust a first oxygen concentration, and no breakdown of NOx is intended to take place. In a second measuring cell, which is joined to the first through a diffusion barrier, the oxygen content is reduced further by a second oxygen ion pump current. The breakdown of NOx at a measuring electrode leads to a third oxygen ion pump current, which is a measure of the NOx concentration. The entire measuring detector is, in such a case, brought to an elevated temperature, for example, 750° C., by an electrical heater.

This NOx measuring detector is a typical example of a gas sensor in which the measuring accuracy depends very strongly on the operating temperature.

It is therefore absolutely necessary to measure the operating temperature in such gas sensors.

One prior art measuring method makes use, in the aforementioned NOx measuring detector, of the temperature-dependent impedance of the measuring cells. By the imposition of an alternating current and corresponding current measurement, it is possible to determine the impedance and, hence, the sensor temperature. Although such a method is relatively straightforward to implement, it, nevertheless, has disadvantages in the event of sensor aging, which leads to a long-term change in the impedance, which is directly perceptible as a temperature error. A further problem with the method is that the measuring signal, i.e., the third oxygen ion pump current, may become vitiated when the alternating current is superimposed on it for the measurement.

Another approach utilizes the fact that the resistance of a resistive heating element is temperature-dependent. It is, therefore, possible to connect a measuring resistor into the incoming line of the resistive heating element, and to determine the voltage drop across it, in order to calculate the current flowing through the resistive heating element. Together with the feed voltage of the resistive heating element, the resistance is obtained. In such a two-point measurement, however, the measuring errors due to the concomitant measurement of the incoming line resistances is unacceptably high.

A further prior art method involves four-point measurement of the resistance, as disclosed for example by Tietze, Schenk, "Halbleiter-Schaltungstecknik" [Semiconductor circuit technology] 9th edition, Springer, 1989, pp. 891 et seq. Such four-point measurement, however, requires a voltage tap directly at the contacts of the resistive heating element, which, for most gas sensors, is precluded as being an unacceptably high outlay.

SUMMARY OF THE INVENTION

It is accordingly an object of the invention to provide a drive circuit and drive method for a gas sensor that overcomes the hereinafore-mentioned disadvantages of the heretofore-known devices and methods of this general type and that permit accurate temperature measurement of a gas sensor through the resistance measurement of a resistive heating element, while not entailing the outlay of a four-point measurement.

With the foregoing and other objects in view, there is provided, in accordance with the invention, a drive circuit for a gas sensor having a resistive heating element with an incoming line branch and an outgoing line branch connected to a reference potential, including a feed voltage source producing a feed voltage, a supply branch having the feed voltage applied thereto, a first controllable switching element connected to the supply branch and to the incoming line branch of the heating element, a measuring voltage source, a second controllable switching element connected to the measuring voltage source, a measuring resistor having a first side with a first potential, the first side connected to the second switching element, and a second side with a second potential, the second side connected to the supply branch, a current heating path flowing, when the first switching element is turned on, from the supply branch through the first switching element, the incoming line branch of the heating element, the heating element, and the outgoing line branch to the reference potential, and a measuring current path leading from the measuring voltage source through the second switching element and the measuring resistor into the supply branch, the measuring current path being closed when the first switching element is turned off and the second switching element is turned on, and a measuring device having a first measuring pin connected to the first side of the measuring resistor for tapping off the first potential, a second measuring pin connected to the second side of the measuring resistor for tapping off the second potential, and a third measuring pin connected to the outgoing line branch of the heating element for tapping off a potential at the outgoing line branch.

According to the invention, a three-point measurement is carried out. To measure the resistance of the resistive heating element, a measuring current is, in this case, passed through a measuring resistor and fed into the incoming line branch of the resistive heating element.

In the following description, the term "incoming line branch" will be used to refer to the line branch that leads from the feed voltage to the resistive heating element. The term "outgoing line branch" will be used to refer to that line branch that leads from the resistive heating element to the reference potential.

The heating current is turned off during the measuring phase. The measuring current that is driven by a measuring voltage is recorded through corresponding taps at the measuring resistor. The potential is tapped directly from where the resistive heating element makes contact on the outgoing line branch side so that it is possible to calculate the resistance from the potential difference between such potential and the potential of the measuring signal voltage, together with the measuring current.

In such a case, the incoming line resistance of the outgoing line branch is not concomitantly measured because, due to the potential tap at the start of the outgoing line branch, it is possible to determine the latter's line resistance. It can be set approximately equal to the line resistance of the incoming line branch, which provides the possibility, in an advantageous refinement, of correcting the resistance of the resistive heating element with respect to the line resistances of the incoming line branch and the outgoing line branch.

Controlled switching elements are provided in the drive circuit according to the invention, so that it is possible to switch the measuring current and the heating current.

Because a suitable measuring voltage is used, the direct measurement of the feed voltage may furthermore be obviated. Such a configuration avoids measuring errors and reduces the equipment outlay. Otherwise, it would be necessary to match the feed voltage to the normal input voltage range of an available measuring device, for example, to the input voltage range of AD converters.

Another advantage is that the measuring resistor no longer carries the heavy heating current. It can, therefore, be configured with high impedance, which has a positive effect on the accuracy. Furthermore, the dissipated heat loss is smaller in this case, which has a positive effect on the aging of the measuring resistor and, therefore, in turn, on the accuracy of the measurement. Furthermore, the internal heating of the drive circuit is reduced.

In accordance with another feature of the invention, the incoming line branch of the heating element has an incoming line contact, runs from the first switching element to the incoming line contact, and has a connection node to which at least one of the first and second sides of the measuring resistor is connected.

Because, during the heating phase in the drive circuit according to the invention, the measuring resistor is at the potential of the feed voltage, it is necessary to ensure that, when AD converters are used to determine the voltage drop across the measuring resistor, the maximum allowable input voltage of these AD converters is not exceeded. To protect the converters, they are preferably set to a protective voltage through corresponding diodes and a controlled switching element during the heating phase so that the voltage difference applied to the AD converters is reduced to a tolerable amount. Nevertheless, another solution is conceivable that, in the heating phase, sets the AD converter ports to a suitable protective voltage, for example, by a special integrated circuit.

In accordance with a further feature of the invention, there is provided a protective circuit for connecting the first measuring pin; the second measuring pin; and the third measuring pin to a protective voltage, the protective circuit connected to the first measuring pin; the second measuring pin; and the third measuring pin.

In accordance with an added feature of the invention, the protective circuit has a protective voltage generator providing a protective voltage, current limiting resistors, diodes, and a third switching element. Each of the first, second, and third measuring pins are respectively connected to the third switching element through one of the current limiting resistors and one of the diodes and the protective circuit is connected to a protective voltage and selectively turns the protective voltage on and off.

In accordance with an additional feature of the invention, the measuring voltage source is a measuring voltage generator producing a measuring voltage from the feed voltage.

The coordination of the measuring phases and the heating phases may be carried out by a microprocessor, although an analog circuit or programmable logic are also conceivable.

In accordance with yet another feature of the invention, the measuring device has a microprocessor with AD converter ports.

In accordance with yet a further feature of the invention, the AD converter ports drive at least one of the first, second, and third switching elements.

In accordance with yet an added feature of the invention, the measuring device has a first differential amplifier with first and second inputs, the first measuring pin is the first input, and the second measuring pin is the second input.

In accordance with yet an additional feature of the invention, the measuring device has a differential amplifier with first and second inputs, the second measuring pin is the first input, and the third measuring pin is the second input.

In accordance with again another feature of the invention, the measuring device has a first differential amplifier with first and second inputs and a second differential amplifier with third and fourth inputs, the first measuring pin is the first input, the second measuring pin is the second input and the third input, and the third measuring pin is the fourth input.

With the objects of the invention in view, there is also provided a method for driving a gas sensor having a resistive heating element, including the steps of during heating phases, applying a heating current flowing in a heating current circuit to the heating element, during in measuring phases, applying a measuring current smaller than the heating current and flowing in a measuring current circuit to the heating element by a given measuring voltage, the measuring current circuit and the heating current circuit being formed in given sections by same conductors, determining a resistance of the heating element from the measuring current and the measuring voltage, alternating the measuring phases and the heating phases, deriving the temperature from the resistance of the heating element, and taking the derived temperature into account during a configuration of the heating phases, and measuring a voltage drop during the measuring phase in at least a part of the given sections, ascertaining therefrom a corresponding line resistance, and taking the line resistance into account when determining the resistance of the heating element.

In accordance with again a further mode of the invention, a line resistance of all of the given sections is deduced from the line resistance of the part of the given sections to obtain a corrected line resistance and the corrected line resistance is taken into account when the measuring phases and the heating phases are alternated, the temperature from the resistance of the heating element is derived, and the derived temperature is taken into account during the configuration of the heating phases.

In accordance with again an added feature of the invention, a line resistance of all of the given sections is deduced from the line resistance of the part of the given sections to obtain a corrected line resistance and the corrected line resistance is taken into account in step (d).

In accordance with a concomitant mode of the invention, a duration of a measuring phase is selected to be less than a thermal time constant of the heating element.

Because the resistive heating element is not heated during the measuring phase, the measuring phase should be configured so as to be short compared with the thermal time constant of the resistive heating element, or of the heated gas sensor, in order to minimize any measurement vitiation due to cooling in the unheated measuring phase.

Other features that are considered as characteristic for the invention are set forth in the appended claims.

Although the invention is illustrated and described herein as embodied in a drive circuit and drive method for a gas sensor, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
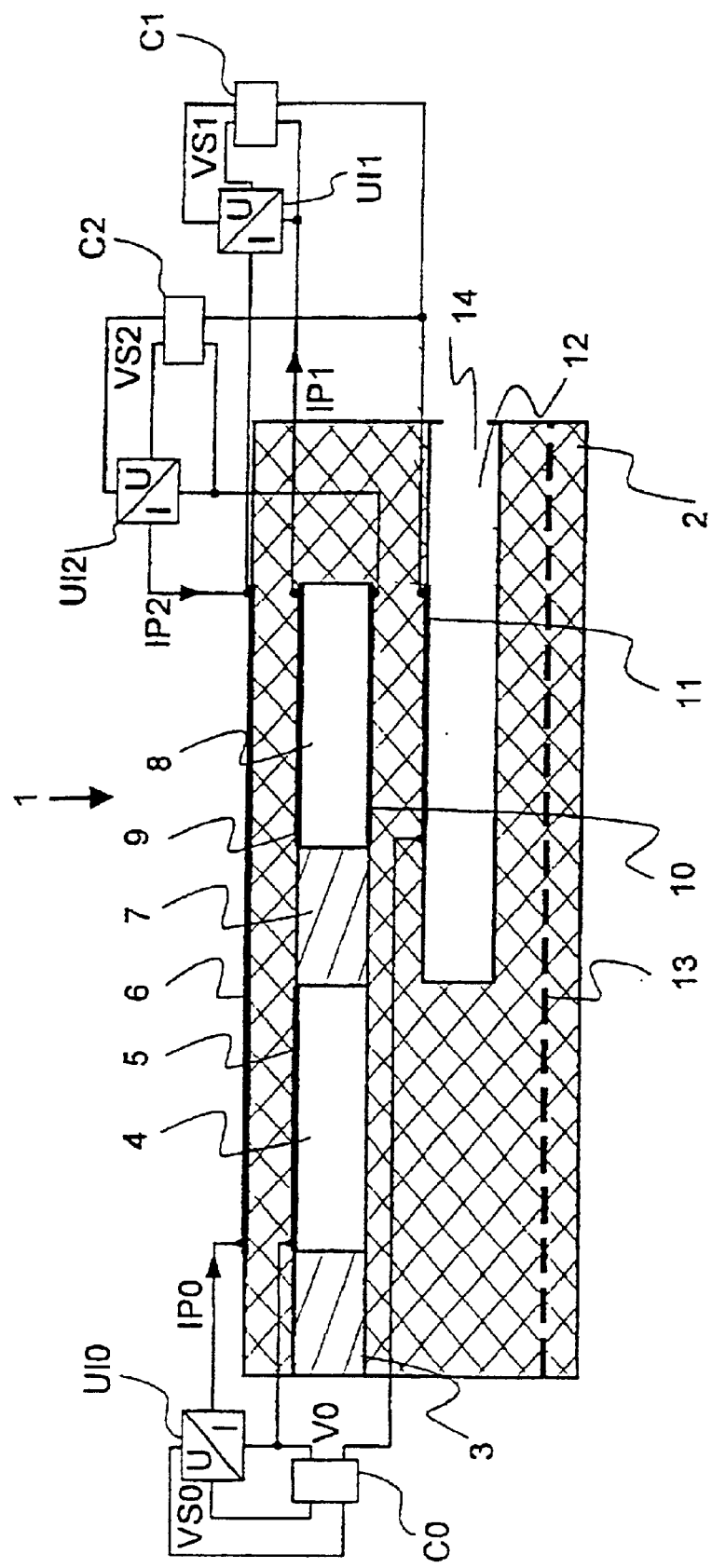
FIG. 1 is a block circuit diagram and a cross-sectional view of a NOx measuring detector according to the invention.

Referring now to the figures of the drawings in detail and first, particularly to FIG. 1 thereof, there is shown a section through a NOx measuring detector 1. The NOx measuring detector 1 is resistively heated, and is used to measure the NOx concentration in the exhaust gas of an internal combustion engine. It is exemplary of a gas sensor for which the drive circuit according to the invention, or the method according to the invention, is intended.

The measuring detector 1 is of a solid-state electrolyte 2, in this case $ZrO_2$, and receives, through a diffusion barrier 3, the exhaust gas to be measured, whose NOx concentration is to be determined. The exhaust gas diffuses through the diffusion barrier 3 into a first measuring cell 4. The oxygen content in the measuring cell 4 is measured by tapping a Nernst voltage between a first electrode 5 and a reference electrode 11 exposed to ambient air. In the embodiment of FIG. 1, the reference electrode 11 is disposed in an air channel 12 that ambient air enters through an opening 14.

The tapped Nernst voltage is sent to a controller C0, which provides a control voltage VS0. This drives a voltage-controlled current source UI0, which drives a first oxygen ion pump current IP0 through the solid-state electrolyte 2 of the measuring detector 1 between the first electrode 5 and an outer electrode 6. As such, a predetermined oxygen concentration is set up in the first measuring cell 4. The concentration is measured through the Nernst voltage between the electrode 5 and the reference electrode 11 so that the control loop of the controller C0 is closed.

Thus, the described circuit configuration adjusts a predetermined oxygen concentration in the first measuring cell 4. The second measuring cell 8 is joined to the first measuring cell 4 through a further diffusion barrier 7. The gas present in the first measuring cell 4 diffuses through this diffusion barrier 7 into the second measuring cell 8. A second oxygen concentration is adjusted in the second measuring cell 8 by a circuit configuration. To that end, a second Nernst voltage is tapped between a second electrode 9 and the reference electrode 11, and is sent to a controller C1 that provides a second control voltage VS1, with which a second voltage-controlled current source UI1 is driven. The circuit configuration for driving the oxygen ion pump current IP1 from out of the second measuring cell 8, hence, corresponds to the circuit configuration for the first measuring cell 4.

The circuit configuration drives the oxygen ion pump current IP1 such that a predetermined oxygen concentration is adjusted in the second measuring cell 8.

The oxygen concentration is, in such a case, selected so that NOx is unaffected by the processes that occur, and, in particular, no breakdown takes place. The NOx is then pumped at the measuring electrode 10, which may be catalytically configured, from the measuring electrode 10 to the outer electrode 6 in a third oxygen ion pump current IP2, which is, hence, a measure of the NOx concentration in the measuring cell 8 and, hence, in the exhaust gas to the measured.

Like the previous pump currents, the pump current IP2 is driven by a voltage-controlled current source UI2, whose control voltage VS2 is set by a controller C2 that taps the Nernst voltage between that of the measuring electrode 10 and the reference electrode 11 and sets up a predetermined Nernst voltage by setting the control voltage VS2.

Figure 2:
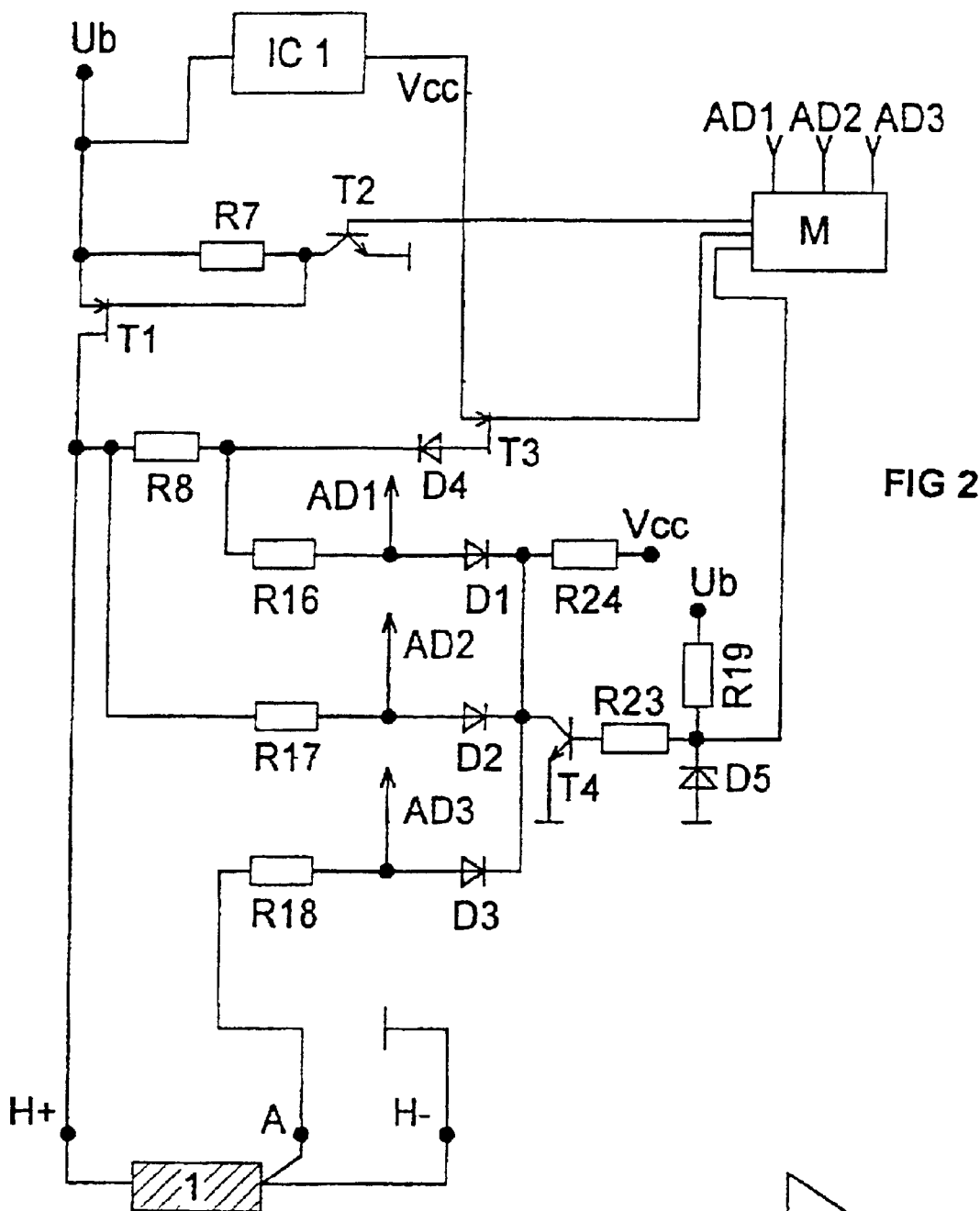
FIG. 2 is a block and schematic circuit diagram for the measuring detector of FIG. 1.

The heater 13 of FIG. 1 is embodied as a resistor 1a in the circuit of FIG. 2. The resistor 1a, i.e., the heater 13, has three terminals H+, H−, and A. The resistor 1a is located between the terminals H+ and H−, which are the terminals for the incoming line branch and the outgoing line branch, respectively. The tap A is used for the following conduct of a three-point measurement. The incoming line contact H+ of the resistor 1a is connected through a transistor T1 to a battery voltage Ub. The control input of the transistor T1 is connected to the collector of a transistor T2 and, through a resistor R7, also to the battery voltage Ub. Because the transistor T2 is set through its emitter to the reference potential, the battery voltage Ub can be switched through to the transistor T1 by driving the base, which is joined to a microprocessor M.

The resistor 1a is furthermore connected through its outgoing line contact H− to the reference potential. If the transistor T1 is turned on, then a heating current flows from the incoming line branch through H+ to the resistor 1a, and from there through H− to the reference potential.

Then, to be able to determine the value of the resistor 1a, a measuring resistor R8 to which it is possible to apply, through a transistor T3, a measuring voltage $V_{cc}$ that is produced by a 5 V generator IC1 from the battery voltage Ub, is connected between the transistor T1 and the incoming line contact H+ at the incoming line branch. The transistor T3 is, in turn, driven at its base by the microprocessor M. A diode D4 between the collector of the transistor T3 and the measuring resistor R8 prevents any undesired return flow of current. The potential is sampled before and after the measuring resistor R8 by an AD converter port AD1 and AD2, respectively. To prevent (when the transistor T3 is off and the transistor T1 is on, i.e., when the heating current is flowing) the AD converter ports from being taken to a voltage that is significantly greater than the maximum allowable input voltage, they are set to an increased voltage, for example, 1.5 V, and thereby protected, through a diode D1 and D2, respectively, and a resistor R16 and R17, respectively, which are connected in series with the respective AD converter port AD1 and AD2, respectively, by a transistor T4 to whose collector the cathodes of the diodes D1 and D2 are connected. The base of the transistor T4 is driven by the microprocessor M, with a circuit made up of a series-connected resistor R23 and a resistor R19 set to the battery voltage Ub, as well as a Zener diode set to the reference potential being provided therebetween.

The tap A at the start of the outgoing line branch of the resistor 1a is applied through a resistor R18 to an AD converter port AD3, which is likewise connected through a diode D3 to the collector of the transistor T4.

For heating, the transistor T1 is turned on by the microprocessor M. At the same time, the AD converter ports AD1–AD3 are protected against overvoltage and the heating current flows through the resistor 1a, by driving the transistor T4 and setting the AD converter ports to a protective voltage. For measuring the resistance, through driving of the transistor T2, T3, and T4 by the microprocessor M, the transistor T1 is turned off and the AD converter ports AD1–AD3 are enabled. The potential difference between AD2 and AD3 gives the measuring voltage $V_{cc}$. The potential difference between AD1 and AD2, together with the resistance of R8 and the measuring voltage $V_{cc}$, gives the measuring current that flows in this case. Because no current flows in this voltage measurement, the resistors R17 and R18 do not need to be taken into account.

The potential difference between AD3 and the reference potential makes it possible to determine the line resistance in the approaching line branch. If the same line resistance is taken for the incoming line branch, a very exact calculation of the value of the resistor 1a is permitted. Optionally, the ratio of the line resistances of the incoming and outgoing line branches may be determined once, for example, exemplarily, and further taken into account.

Naturally, the duration of the measurement should be selected to be short compared with the thermal time constant of the resistive heater 13, or of the NOx measuring detector, in order to avoid vitiating cooling during the resistance measurement.

From the value of the resistor 1a, the temperature of the resistor 1a and, therefore, of the heater 13 can be determined in a conventional way.

Through the mutual switching of T1 with T4 and T3, the direct measurement of the battery voltage Ub can be obviated.

Figure 3:
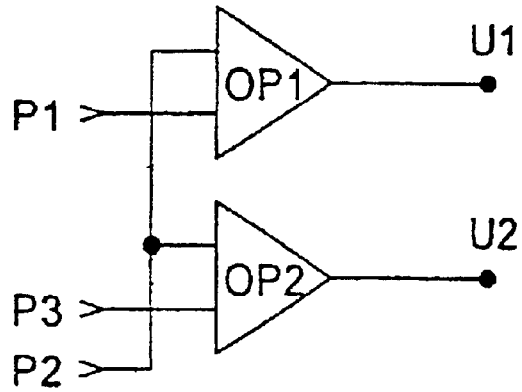
FIG. 3 is a schematic circuit diagram of an element of a modified embodiment of the circuit of FIG. 2.

If it is desired to obviate the microprocessor M then, instead of the AD converter ports AD1–AD3, it is also possible to provide measuring pins P1–P3 and to join them to differential amplifiers OP1 and OP2, as represented in FIG. 3. In such a case, the difference between P1 and P2 is sent to a first differential amplifier OP1, at whose output the measuring voltage U1 represents a measure of the measuring current; the measuring pins P2 and P3 are sent to a second operational amplifier OP2, at whose output the measuring voltage U2 is a measure of the measuring voltage. It is also possible to provide only the differential amplifier OP1, and to send its output to an AD converter port. Such a configuration eliminates the need for one AD converter port. However, the measuring voltage then needs to be determined based upon $V_{cc}$ (corrected by the voltage drop across the measuring resistor R8) and it can no longer be measured.

The simplified circuit with two differential amplifiers does not then make it possible to ascertain the line resistance in the outgoing line branch.

I claim:

1. A drive circuit for a gas sensor having a resistive heating element with an incoming line branch and an outgoing line branch connected to a reference potential, comprising;
    a feed voltage source producing a feed voltage;
    a supply branch having said feed voltage applied thereto;
    a first controllable switching element connected to said supply branch and to the incoming line branch of the heating element;
    a measuring voltage Source;
    a second controllable switching element connected to said measuring voltage source;
    a measuring resistor having:
        a first side with a first potential, said first side connected to said second Switching element; and
        a second side with a second potential, said second side connected to said supply branch;
    a current heating path flowing, when said first switching element is turned on, from said supply branch through said first switching element, the incoming line branch of the heating element, the heating element, and the outgoing line branch to the reference potential; and
    a measuring current path leading from said measuring voltage source through said second switching element and said measuring resistor into said supply branch, said measuring current path being closed when said first switching element is turned off and said second switching element is turned on; and
    a measuring device having:
        a first measuring pin connected to said first side of said measuring resistor for tapping off said first potential;
        a second measuring pin connected to said second side of said measuring resistor for tapping off said second potential; and
        a third measuring pin connected to the outgoing line branch of the heating element for tapping off a potential at the outgoing line branch.

2. The drive circuit according to claim 1, wherein the incoming line branch of the heating element:
    has an incoming line contact;
    runs from said first switching element to the incoming line contact; and
    has a connection node to which at least one of said first and second sides of said measuring resistor is connected.

3. The drive circuit according to claim 1, including a protective circuit for connecting said first measuring pin; said second measuring pin; and said third measuring pin to a protective voltage, said protective circuit connected to said first measuring pin, said second measuring pin; and said third measuring pin.

4. The drive circuit according to claim 3, wherein:
    said protective circuit has:
        a protective voltage generator providing a protective voltage;
        current limiting resistors;
        diodes; and
        a third switching element;
    each of said first, second, and third measuring pins are respectively connected to said third switching element through one of said current limiting resistors and one of said diodes; and
    said protective circuit is connected to a protective voltage and selectively turns the protective voltage on and off.

5. The drive circuit according to claim 1, wherein said measuring voltage source is a measuring voltage generator producing a measuring voltage from said feed voltage.

6. The drive circuit according to claim 1, wherein said measuring device has a microprocessor with AD converter ports.

7. The drive circuit according to claim 1, wherein said AD converter ports drive at least one of said first, second, and third switching elements.

8. The drive circuit according to claim 1, wherein:
said measuring device has a first differential amplifier with first and second inputs;
said first measuring pin is said first input; and
said second measuring pin is said second input.

9. The drive circuit according to claim 1, wherein:
said measuring device has a differential amplifier with first and second inputs;
said second measuring pin is said first input; and
said third measuring pin is said second input.

10. The drive circuit according to claim 1, wherein:
said measuring device has:
a first differential amplifier with first and second inputs; and
a second differential amplifier with third and fourth inputs;
said first measuring pin is said first input;
said second measuring pin is said second input and said third input; and
said third measuring pin is said fourth input.

11. A method for driving a gas sensor having a resistive heating element, which comprises:
a) providing the drive circuit according to claim 1;
b) during heating phases, applying a heating current flowing in a heating current circuit to the heating element;
c) during measuring phases, applying a measuring current smaller than the heating current and flowing in a measuring current circuit to the heating element by a given measuring voltage;
d) measuring, with a measuring device,
the first potential at the first side of the measuring resistor;
the second potential at the second side of the measuring resistor; and
a potential at the outgoing line branch of the heating element;
and determining a resistance of the heating element from the measuring current and the measuring voltage; and measuring a voltage drop during the measuring phase, ascertaining therefrom a corresponding line resistance, and taking the line resistance into account when determining the resistance of the heating element;
e) alternating the measuring phases and the heating phases, deriving the temperature from the resistance of the heating element, and taking the derived temperature into account during a configuration of the heating phases.

12. The method according to claim 11 wherein the measuring current circuit and the heating current circuit is formed in given sections by the same conductors, and the method further comprises:
deducing a line resistance of all of the given sections from the line resistance of the part of the given sections to obtain a corrected line resistance; and
taking into account the corrected line resistance when the measuring phases and the heating phases are alternated, the temperature from the resistance of the heating element is derived, and the derived temperature is taken into account during the configuration of the heating phases.

13. The method according to claim 11 wherein the measuring current circuit and the heating current circuit is formed in given sections by the same conductors, and the method further comprises:
wherein the measuring current circuit and the heating current circuit is formed in given sections by the same conductors;
deducing a line resistance of all of the given sections from the line resistance of the part of the given sections to obtain a corrected line resistance; and
taking into account the corrected line resistance in step (e).

14. The method according to claim 11, which further comprises selecting a duration of a measuring phase to be less than a thermal time constant of the heating element.

15. In combination with a circuit for a gas sensor with a resistive heating element having an incoming line branch and an outgoing line branch connected to a reference potential, a gas sensor drive circuit, comprising:
a feed voltage source producing a feed voltage;
a supply branch having said feed voltage applied thereto;
a first controllable switching element connected to said supply branch and to the incoming line branch of the heating element;
a measuring voltage source;
a second controllable switching element connected to said measuring voltage source;
a measuring resistor having:
a first side with a first potential, said first side connected to said second switching element; and
a second Bide with a second potential, said second side connected to said supply branch;
a current heating path flowing, when said first switching element is turned on, from said supply branch through said first switching element, the incoming line branch of the heating element, the heating element, and the outgoing line branch to the reference potential; and
a measuring current path leading from said measuring voltage source through said second switching element and said measuring resistor into said supply branch, said measuring current path being closed when said first switching element is turned off and said second switching element is turned on; and
a measuring device having:
a first measuring pin connected to said first side of said measuring resistor for tapping off said first potential;
a second measuring pin connected to said second side of said measuring resistor for tapping off said second potential; and
a third measuring pin connected to the outgoing line branch of the heating element for tapping off a potential at the outgoing line branch.

* * * * *